US00PP29889P3

(12) United States Plant Patent

Maria de Jong

(10) Patent No.: US PP29,889 P3
(45) Date of Patent: Nov. 27, 2018

(54) CHERRY LAUREL PLANT NAMED 'JONG1'

(50) Latin Name: *Prunus laurocerasus*
Varietal Denomination: Jong1

(71) Applicant: Cornelis Henricus Maria de Jong, Biezenmortel (NL)

(72) Inventor: Cornelis Henricus Maria de Jong, Biezenmortel (NL)

( * ) Notice: Subject to any disclaimer, the term of this patent is extended or adjusted under 35 U.S.C. 154(b) by 0 days.

(21) Appl. No.: 15/530,750

(22) Filed: Feb. 22, 2017

(65) Prior Publication Data

US 2018/0242487 P1 Aug. 23, 2018

(51) Int. Cl.
*A01H 5/00* (2018.01)
*A01H 6/74* (2018.01)

(52) U.S. Cl.
USPC ..... Plt./226
CPC ..... *A01H 6/7427* (2018.05)

(58) Field of Classification Search
USPC ..... Plt./226
CPC ..... A01H 5/00; A01H 5/02
See application file for complete search history.

*Primary Examiner* — Kent L Bell
(74) *Attorney, Agent, or Firm* — Barbara Campbell; Cochran Freund & Young LLC

(57) ABSTRACT

A new cherry laurel plant particularly distinguished by being winter hardy, having healthy growth, and a compact and bushy habit, is disclosed.

2 Drawing Sheets

Genus and species: *Prunus laurocerasus.*
Variety denomination: 'Jong1'.

BACKGROUND OF THE NEW PLANT

The present invention comprises a new and distinct variety of Cherry laurel plant, botanically known as *Prunus laurocerasus*, and hereinafter referred to by the variety name 'Jong1'. 'Jong1' originated from an open-pollination conducted in Biezenmortel, The Netherlands in 2006 between un-named and unpatented *Prunus laurocerasus* plants.

The seeds from the open-pollination were sown and plants were grown outdoors for evaluation, where an individual plant designated 'Jong1' was selected from the group of plants in Biezenmortel, The Netherlands in May 2007. In October 2007, 'Jong1' was first vegetatively propagated by softwood cuttings. 'Jong1' was found to reproduce true to type in successive generations of asexual propagation via softwood cuttings.

SUMMARY

The following are the most outstanding and distinguishing characteristics of this new variety when grown under normal horticultural practices in The Netherlands.

1. Winter hardy;
2. Healthy growth; and
3. Compact and bushy habit.

DESCRIPTION OF THE PHOTOGRAPHS

This new cherry laurel plant is illustrated by the accompanying photographs which show the plant's overall plant habit including form, and foliage. The photographs are of a two-year-old plant grown outdoors in The Netherlands in March 2015. The colors shown are as true as can be reasonably obtained by conventional photographic procedures.

Figure 1:
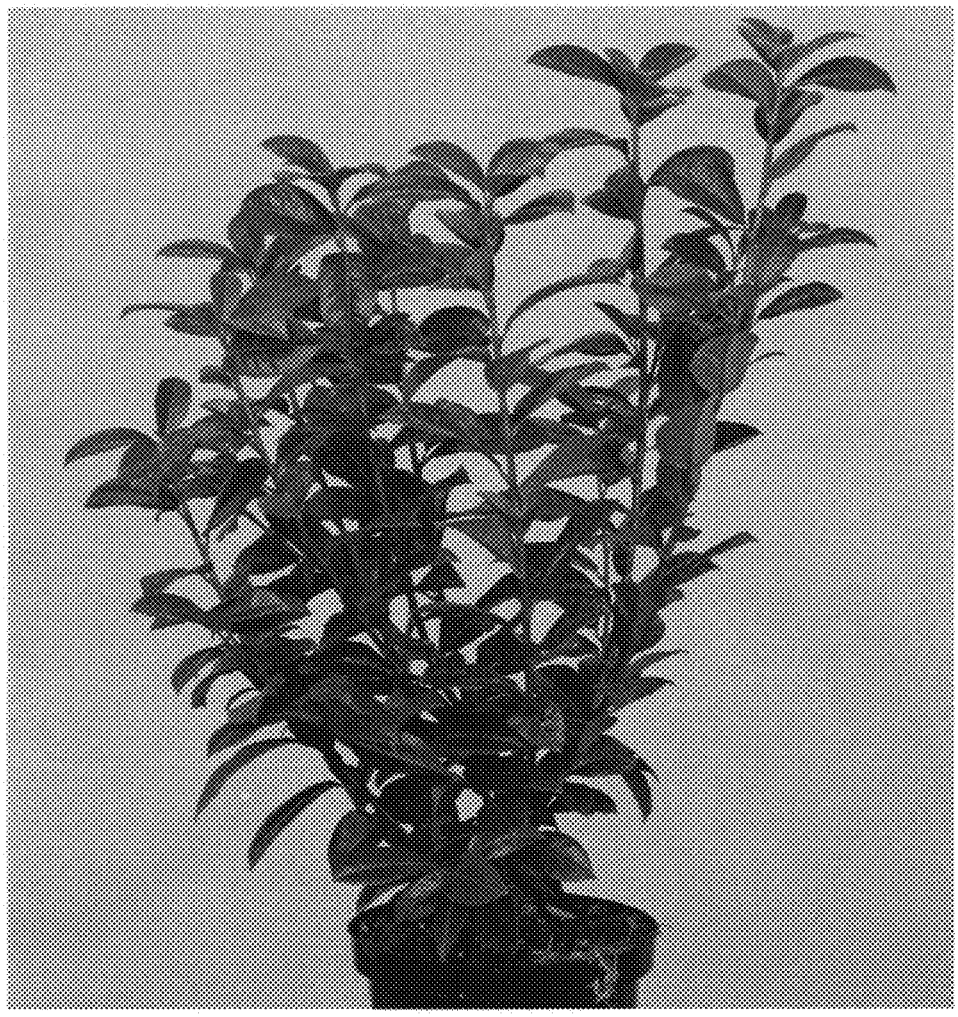
Figure 2:
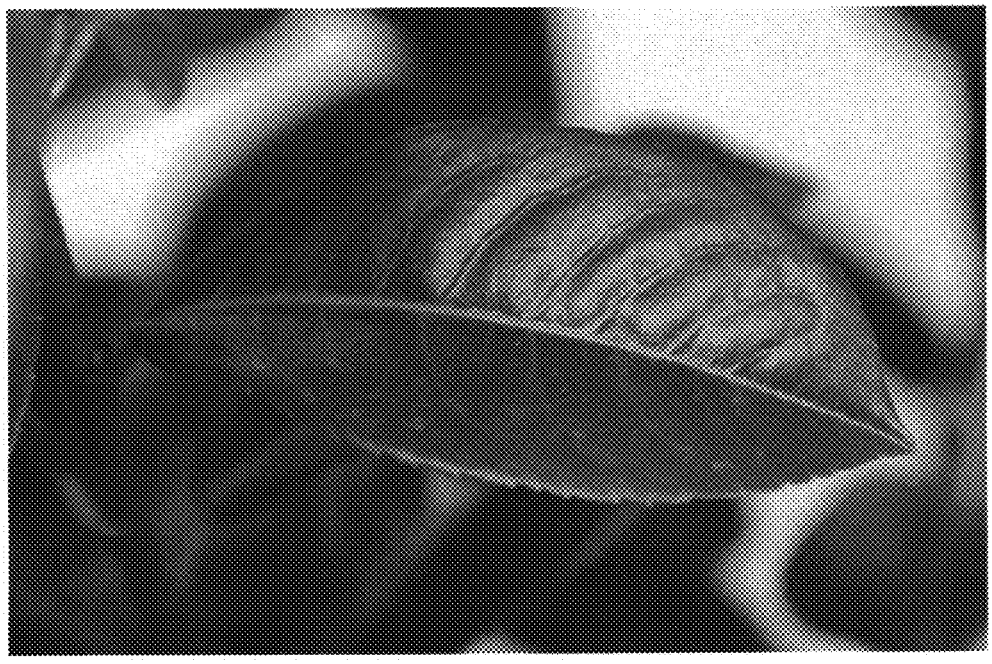

FIG. 1 shows the overall plant habit of 'Jong1'.
FIG. 2 shows a close-up of an individual leaf.

DESCRIPTION OF THE NEW VARIETY

The following detailed descriptions set forth the distinctive characteristics of 'Jong1'. The data which define these characteristics were collected from asexual reproductions carried out in The Netherlands. Data was collected on two-year-old plants grown outdoors in The Netherlands in March 2015. The range of day temperatures was 10° C. to 25° C. and the range of night temperatures was 6° C. to 14° C. Color references are to The R.H.S. Colour Chart of The Royal Horticultural Society of London (R.H.S.), 5$^{th}$ edition (2007).

Classification:
- *Family.*—Rosaceae.
- *Botanical.*—*Prunus laurocerasus.*
- *Common.*—Cherry laurel; English laurel.
- *Designation.*—'Jong1'.

Plant:
- *Type.*—Perennial, evergreen shrub.
- *Time to produce a finished plant.*—About 2.5 years from rooted cuttings.
- *Appropriate container for producing a finished plant.*—1.5 liter containers and larger or field-grown.
- *Plant shape.*—Moderately broad inverted triangle.
- *Growth habit.*—Moderately broad upright.
- *Average plant height.*—60.5 cm.
- *Average plant diameter.*—53.3 cm.
- *Growth rate.*—About 40.0 cm per season as a pot-grown young plant.
- *Vigor.*—Moderately high.
- *High temperature tolerance.*—Unknown, but tolerant to temperatures up to 35° C.
- *Low temperature tolerance.*—Unknown, but at least hardy to USDA Zone 6.

*Disease/pest resistance and susceptibility*.—Not more susceptible to pests and diseases than other varieties of same species.

Branches:

*Habit*.—Moderate.

*Basal branching*.—Present.

*Pinching*.—Not required but will improve branching.

*Number of lateral branches per plant*.—Average is 10.

*Branch length*.—Average is 40.1 cm.

*Branch diameter*.—Average is 4.0 mm.

*Internode length*.—Average is 2.4 cm.

*Appearance and shape*.—Rounded; young branches are slightly angled towards the top; glossy.

*Aspect*.—Lateral stems have an average angle of 40 degrees to the main stem.

*Strength*.—Strong.

*Color*.—Younger branches are RHS 143B; older branches are RHS N199A (Grey-brown).

*Pubescence*.—Absent.

*Texture*.—Smooth.

Leaves:

*General*.—At the base of each leaf, there are an average of 4 glands that are visible on the lower surface, with 2 glands on each side of the main leaf vein; the diameter of each gland is 1.0 cm; the color of each gland is RHS 183D (Greyed-purple); the presence of these glands is typical for this species.

*Arrangement*.—Alternate, single.

*Number of leaves per branch*.—Average is 17.

*Shape*.—Obovate to near elliptic.

*Apex*.—Short apiculate.

*Base*.—Rounded to very short attenuate.

*Margin*.—Slightly revolute; serrate with shallow serrated margins; average of 3 teeth per centimeter.

*Length*.—Average is 8.8 cm.

*Width*.—Average is 4.4 cm.

*Texture*.—Smooth; upper surface is very glossy; lower surface is slightly glossy.

*Venation pattern*.—Pinnate.

*Venation color* (*both upper and lower surfaces*).—RHS 144A (Yellow-green).

*Color*.—Immature: Upper surface: Between RHS 143A (Green) to RHS 144A (Yellow-green). Lower surface: Between RHS 144A (Yellow-green) and RHS 144B (Yellow-green). Mature: Upper surface: Between RHS N137A (Dark-green) to RHS 147A (Yellow-green), but closest to RHS N137A and darker. Lower surface: Between RHS 144A (Yellow-green) and RHS 146B (Yellow-green).

*Petiole*.—Length: Average is 0.9 cm. Diameter: Average is 2.0 mm. Color: RHS 144A (Yellow-green). Durability of foliage to stresses: High. Texture: Smooth.

Flowers/seed/fruit: Not observed to date.

COMPARISON WITH COMMERCIAL VARIETY AND PARENTAL LINES

'Jong1' can be distinguished between the commercial variety 'Antonius' (U.S. Plant Pat. No. 26,314) in Table 1.

TABLE 1

Comparison with Commercial Variety

| Characteristic | 'Jong1' | 'Antonius' |
|---|---|---|
| Internode length | 2.4 cm | 8.0 cm |

'Jong1' can be distinguished from the un-named parental lines in that 'Jong1' has a more compact and bushy plant habit than the parental lines.

I claim:

1. A new and distinct variety of *Prunus laurocerasus* plant designated 'Jong1' as illustrated and described herein.

* * * * *